US00PP12103P2

(12) United States Plant Patent
Lemon

(10) Patent No.: US PP12,103 P2
(45) Date of Patent: Sep. 25, 2001

(54) GERANIUM PLANT NAMED 'SINCERELY YOURS'

(75) Inventor: David Lemon, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/120,155

(22) Filed: Jul. 21, 1998

(51) Int. Cl.[7] ..... A01H 5/00
(52) U.S. Cl. ..... Plt./330
(58) Field of Search ..... Plt./330

(56) References Cited

U.S. PATENT DOCUMENTS

P.P. 5,311 * 10/1984 Hoffman ..... Plt./330
P.P. 6,064 * 12/1987 Winner ..... Plt./330

* cited by examiner

*Primary Examiner*—Bruce R. Campell
*Assistant Examiner*—Wendy A Baker
(74) *Attorney, Agent, or Firm*—Fulwider Patton Lee & Utecht, LLP

(57) ABSTRACT

The cultivar is characterized by the bright clear orange-red flower color with a faint "eye" on select petals on medium green foliage. Its quick rooting time and enhanced production provides for superb cuttings and for quick recovery of the bloom following wet weather or high heat conditions. The cultivar provides a relatively large floret, and an abundant amount of cuttings may be obtained from a single plant.

1 Drawing Sheet

BACKGROUND OF THE NEW PLANT

The present invention comprises a new and distinct cultivar of *Pelargonium×hortorum* known by the varietal name 'Sincerely Yours' (Oglevee No. 3138, Bodger No. 2 GM 256-6). The new variety was discovered in a selective breeding program by David Lemon at Bodger Seeds, Ltd., Lompoc, Calif. The new variety is a selection from the crossing of 'Dark Beauty' with the product from a crossing of 'Bold Apple Blossom' with 'Tango' (U.S. Plant Pat No. 5,933).

The new cultivar was first asexually reproduced by cuttings at Oglevee Ltd., located at 152 Oglevee Lane, Connellsville, Pa., 15425 and has been repeatedly asexually reproduced by cuttings at Oglevee Ltd. in Connellsville, Pa. It has been found to retain its distinctive characteristics through successive propagations.

The new cultivar, was grown in a glass greenhouse in Connellsville, Pa., using full light, 60° Fahrenheit night temperature, 68° Fahrenheit day temperature, and grown in a soilless media using a constant fertilizer of 200–250 parts per million of Nitrogen and Potassium, in full light. The claimed plant was grown from a rooted cutting, potted in a 10 cm pot and exhibited a six week response time from the rooted cutting to a flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted in a 20 cm pot on approximately Jan. 15, 1996 and flowering on approximately Feb. 27, 1996, under full light in the greenhouse, and color readings were taken in the Oglevee office under 200–220 foot candles of cool white fluorescent light using The Royal Horticultural Society of London Colour Chart.

THE PLANT

Classification:
- *Botanical.*—*Pelargonium×hortorum*
- *Commercial.*—Florist's Geranium 'Sincerely Yours' (Florist's geraniums are high quality plants which grow well outdoors).

Form: Medium mound; uniform.
- *Height.*—27–29 cm from the surface of the media.
- *Growth.*—Free basal branching.
- *Strength.*—Free and early flowering, needs no artificial support.

Foliage: Stalked leaf attachment.

Leaves:
- *Size.*—7.5–9.0 cm across when fully expanded.
- *Shape.*—Reniform; cordate base.
- *Margin.*—Crenate.
- *Texture.*—Smooth and pubescent.
- *Color.*—Top: Green Group 137A. Bottom: Green Group 138A. Zone: Although not prominent there is a slight zone in the leaves.
- *Ribs and veins.*—Palmate venation. Color: Yellow-Green Group 145B.

Petioles:
- *Length.*—7.5–9.5 cm.
- *Color.*—Yellow-Green Group 144A.

Stem:
*Color.*—Yellow-Green Group 144B.
*Internode length.*—3.0 cm–4.5 cm.

THE BUD (UMBEL)

This information refers to the stage of development when the peduncle has fully elongated and buds are just showing color.

Shape: Elliptical; cluster. Elliptical refers to the shape of the entire bud cluster. Number of buds per cluster is 25–30.
Size: 4.0—5.0 cm across; umbel depth 3.0–4.0 cm; just showing color.

INFLORESCENCE

Blooming habit: Continuous; free and early flowering; observed number of florets 25–30 per umbel.
Borne: Florets on pedicel; pedicel on peduncle.
Closed florets: Bud Size: Just cracking color, 1.5 cm long.
Size: Fully Open Bloom: 9.5–10.0 cm across.
Open florets:
*Form.*—Ruffled; lower petals stack to give a slight cupped appearance. Semi-double.
*Color.*—Top: white at base to Red Group 40B at middle to Red Group 40A at outer edge, veining of Red Group 40A; on approximately two petals per floret have veining of Red Group 50A that extends to an "eye" in those petals only. Bottom: Red Group 40C with faint veining on two petals and "eye" veining of Red Group 50B. Eye: Red Group 50A with faint "eye" veining of Red Group 50B.
*Petals.*—8 in number.
*Size.*—2.0–2.5 cm across.
*Texture and appearance.*—Smooth, satiny looking, reflective; tonality from distance creates a bright clear orange-red bloom.
Petaloids:
*Quanity.*—2–4 petaloids.
*Shape.*—Irregular; twisted.
*Color.*—Top: Red Group 40B. Bottom: Red Group 40C.
Pedicel:
*Length.*—3.0–4.0 cm.
*Color.*—Yellow-Green Group 144C at base; Greyed Purple Group 185A at flower.
Peduncle:
*Length.*—15.5–17.0 cm long.
Color.—Yellow-Green Group 144A.
Persistence:
*Disease resistance.*—No known special disease resistence compared with other Geraniums.
*Lasting quality.*—Holds large flowers on strong stems.

REPRODUCTIVE ORGANS

Stamens:
*Anthers.*—Length: 2.0–3.0 mm.
*Filaments.*—Length: 7.0–9.0 mm. Color: White at base to orange-red at tips.
*Pollen.*—Golden Brown.
Pistils:
*Number.*—1.
*Length.*—6.0–9.0 mm.
*Stigma.*—Color: red.
*Style.*—Length: 4.0–5.0 mm.
Ovaries:
*Color.*—Green.
*Length.*—3.0 mm.
Fruit: None.

GENERAL CHARACTERISTICS

'Sincerely Yours' is a great improvement over 'Yours Truly' and 'Sincerity', when compared, this new variety has better plant habit and improved cutting production and better rooting time as well as enhanced outdoor performance. 'Sincerely Yours' is a large flower having an orange-red bloom with a faint red eye in select petals.

I claim:

1. A new and distinct variety of Geranium plant, substantially as shown and described.

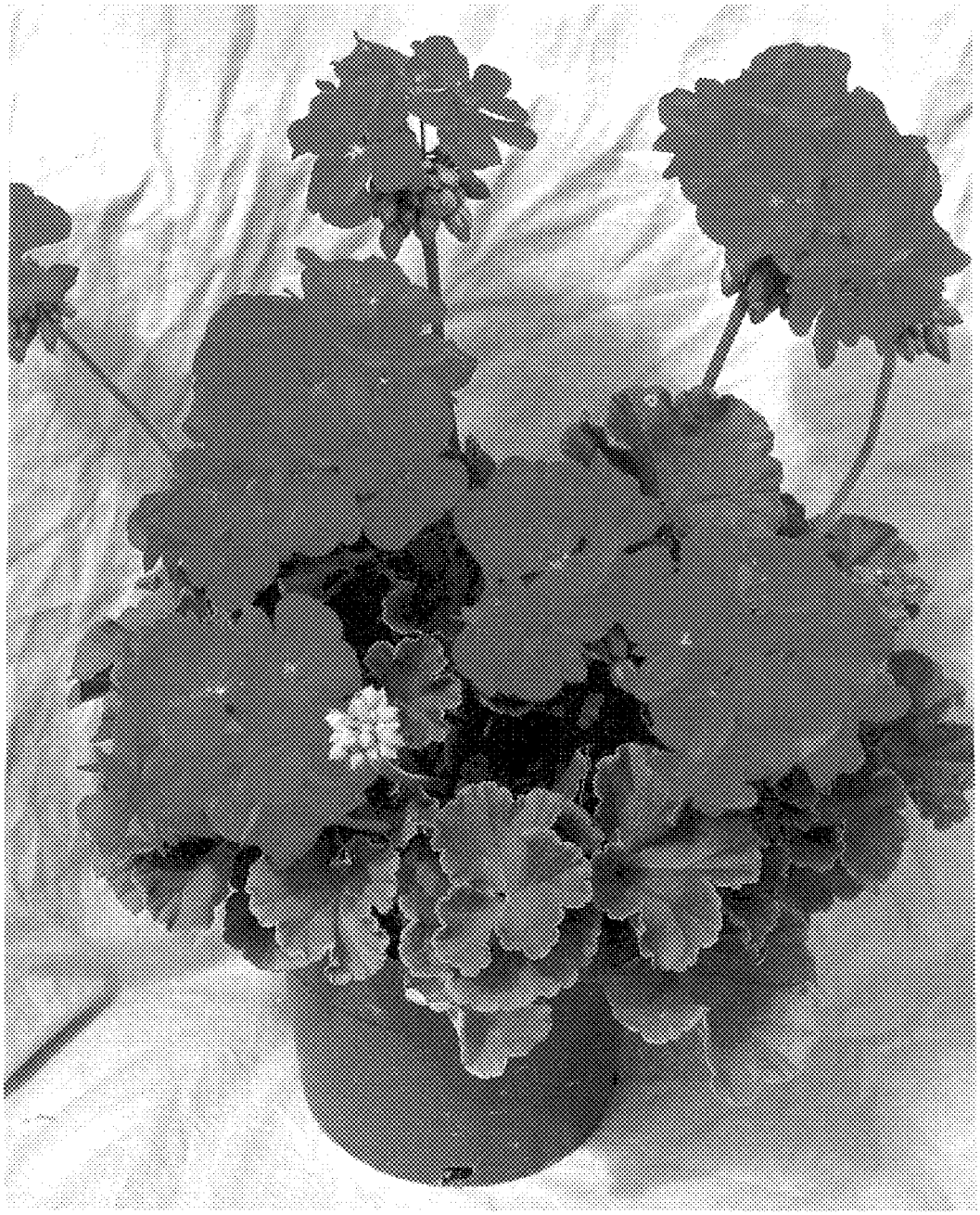

* * * * *